US00PP31598P2

(12) United States Plant Patent
Snijder

(10) Patent No.: US PP31,598 P2
(45) Date of Patent: Mar. 24, 2020

(54) ***PELARGONIUM* PLANT NAMED 'PEQZ0066'**

(50) Latin Name: *Pelargonium peltatum*
Varietal Denomination: PEQZ0066

(71) Applicant: SYNGENTA PARTICIPATIONS AG, Basel (CH)

(72) Inventor: Ronald Christiaan Snijder, Andijk (NL)

(73) Assignee: Syngenta Participations AG, Basel (CH)

( * ) Notice: Subject to any disclaimer, the term of this patent is extended or adjusted under 35 U.S.C. 154(b) by 0 days.

(21) Appl. No.: 16/350,889

(22) Filed: Jan. 29, 2019

(51) Int. Cl.
*A01H 5/02* (2018.01)
*A01H 6/42* (2018.01)

(52) U.S. Cl.
USPC ..... Plt./332
CPC ..... *A01H 6/425* (2018.05)

(58) Field of Classification Search
USPC ..... Plt./332
See application file for complete search history.

*Primary Examiner* — Anne Marie Grunberg
(74) *Attorney, Agent, or Firm* — Dale Skalla

(57) ABSTRACT

A new *Pelargonium* plant named 'PEQZ0066' particularly distinguished by 'red-purplish pink colored inflorescences held above medium-green foliage, large florets on a trailing plant habit.

1 Drawing Sheet

Latin name of the genus and species of the plant claimed: *Pelargonium peltatum*.

Varietal denomination: 'PEQZ0066'.

BACKGROUND OF THE NEW PLANT

The present invention comprises a new *Pelargonium*, botanically known as *Pelargonium peltatum*, and hereinafter referred to by the variety name 'PEQZ0066'.

'PEQZ0066' is a product of a planned breeding program. The new cultivar 'PEQZ0066' has red-purplish pink colored inflorescences held above medium-green foliage, large florets on a trailing plant habit.

'PEQZ0066' originates from a hybridization in a controlled breeding program made in February 2014, in a greenhouse in Amatitlán, Guatemala. The female parent was an unpatented, proprietary plant of *P. peltatum* parentage, identified as 'PEL-AB6077-02' with lighter green colored foliage and a more open plant habit when compared to 'PEQZ0066'.

The male parent of 'PEQZ0066' was an unpatented, proprietary plant of *P. peltatum* parentage, identified as 'PEL-AZ1018-13' with more blue-rose colored florets when compared to 'PEQZ0066'. The resultant seed was sown in December 2014.

'PEQZ0066' was selected as one flowering plant within the progeny of the stated cross in April 2015 in a greenhouse in Enkhuizen, The Netherlands.

The first act of asexual reproduction of 'PEQZ0066' was accomplished when vegetative cuttings were propagated from the initial selection in May 2015 in a greenhouse in Enkhuizen, The Netherlands.

BRIEF SUMMARY OF INVENTION

Horticultural examination of plants grown from cuttings of the plant initiated in June 2015 in Enkhuizen, The Netherlands, and continuing thereafter, has demonstrated that the combination of characteristics as herein disclosed for 'PEQZ0066' are firmly fixed and are retained through successive generations of asexual reproduction.

'PEQZ0066' has not been observed under all possible environmental conditions. The phenotype may vary significantly with variations in environment such as temperature, light intensity, and day length.

A Plant Breeder's Right for this cultivar has not yet been applied for. 'PEQZ0066' has not been made publicly available prior to the effective filing date of this application, notwithstanding any disclosure that may have been made less than one year prior to the effective filing date of this application by the inventor or another who obtained 'PEQZ0066' directly from the inventor.

The following traits have been repeatedly observed and are determined to be the basic characteristics of the new variety. The combination of these characteristics distinguishes this *Pelargonium* as a new and distinct variety.

BRIEF DESCRIPTION OF THE PHOTOGRAPHS

The accompanying photographic drawings show typical flower and foliage characteristics of 'PEQZ0066' with colors being as true as possible with an illustration of this type.

Figure 1:
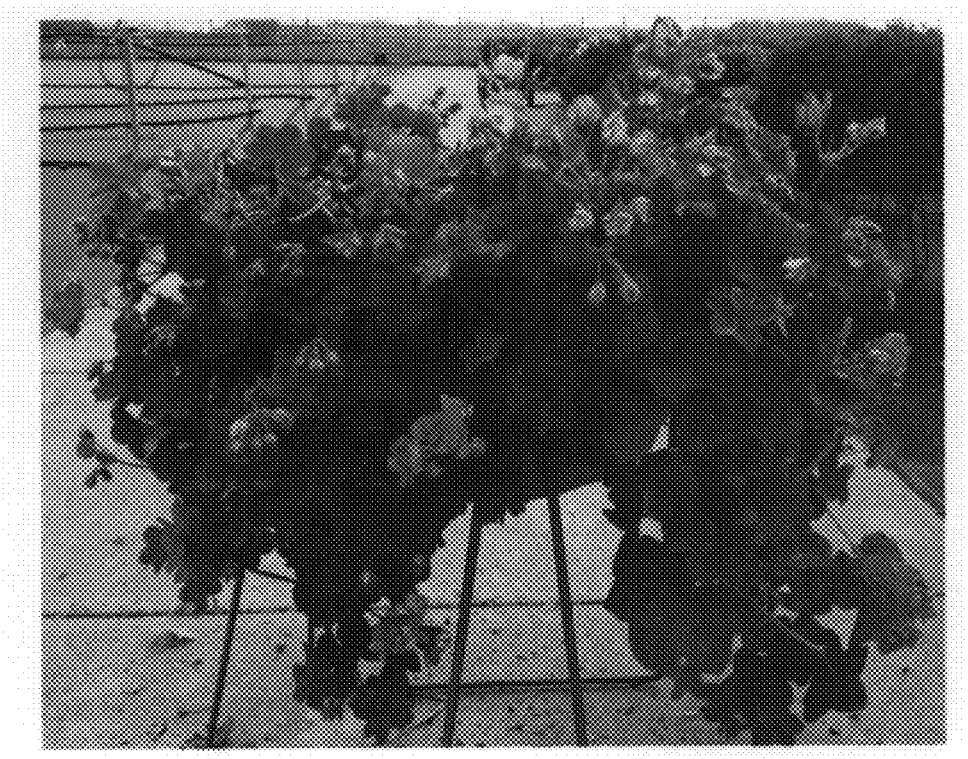
Figure 2:
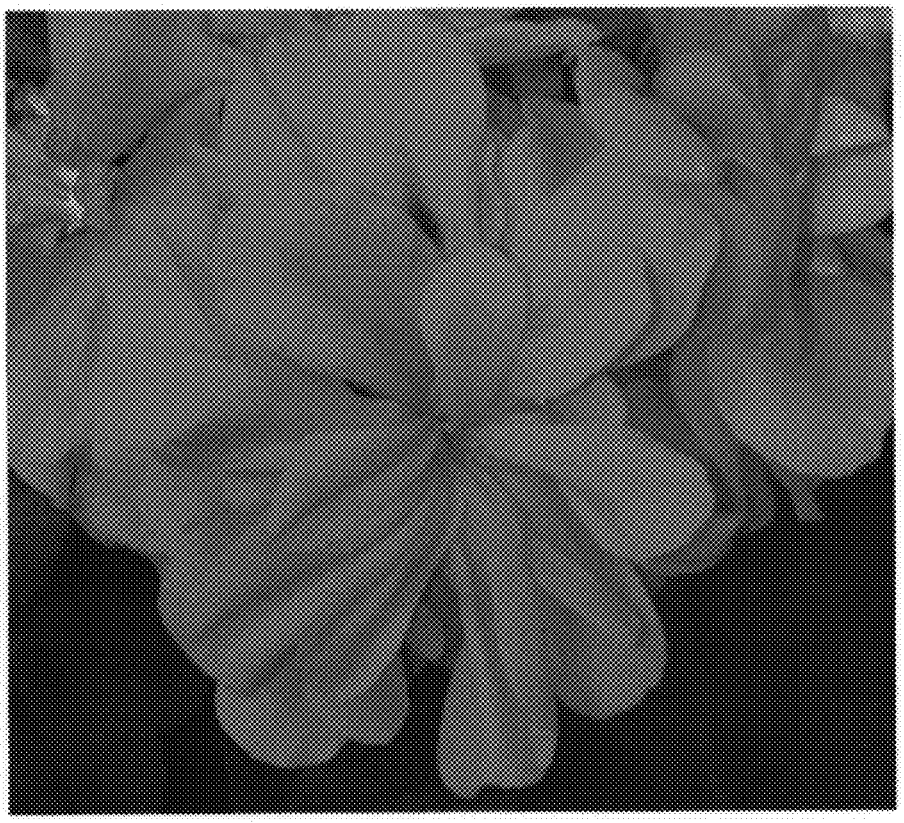

The photographic drawings in FIG. 1, shows a basket with 4 flowering plants of the new variety and in FIG. 2, a close-up of the flower.

DETAILED BOTANICAL DESCRIPTION

The plant descriptions and measurements were taken in Andijk, The Netherlands in September under natural light. These plants were approximately 14 weeks old and were grown in a 1 gallon pots, in a greenhouse trial. The plants shown in the photographs were about 25 weeks old growing in a 10 inch pot in a greenhouse. The photographs were taken in October 2018.

Color references are made to The Royal Horticultural Society Colour Chart (R.H.S.) 2001.

TABLE 1

DIFFERENCES BETWEEN THE NEW VARIETY 'PEQZ0066' AND A MOST SIMILAR VARIETY

| | 'PEQZ0066' | 'Fisrimba' (U.S. Plant Pat. No. 12,355) |
|---|---|---|
| Color of corolla: | Dark pink with tones of violet and purple | Pink with tones of cherry red |
| Number of petals: | 25-35 | 19-21 |
| Color of foliage and high heat condition: | Fading to yellow-light green | Fading to white-yellow |

Plant:
- *Form, growth and habit.*—Upright to semi-trailing.
- *Plant height.*—18-20 cm.
- *Plant height (inflorescence included).*—24-28 cm.
- *Plant width.*—35-40 cm.

Roots:
- *Number of days to initiate roots.*—15-18 days at about 22 degrees C.
- *Number of days to produce a rooted cutting.*—21-23 days at 22 degrees C.
- *Type.*—Fine, fibrous, free branching.
- *Color.*—RHS N155B but whiter.

Foliage:
- *Immature leaf, color upper surface.*—Between RHS 137B/C and RHS 144A.
- *Immature leaf, lower surface.*—Between RHS 137C and RHS 138B.
- *Mature leaf, color upper surface.*—Between RHS 137A/B and RHS 144A.
- *Mature leaf, color lower surface.*—Closest to RHS 137C and RHS 138B.
- *Length.*—4.5-6.0 cm.
- *Width.*—7.5-9.0 cm.
- *Shape.*—Orbicular, with wavy lobs.
- *Base shape.*—Cordate, heart-shaped.
- *Apex shape.*—Rounded, waved margins.
- *Margin.*—Wavy, undulate margins.
- *Texture upper side.*—Pilose.
- *Texture lower side.*—Pillose.
- *Leaf zonation color.*—RHS 202A (weak zonation).
- *Color of veins, upper surface.*—Closest to RHS 144A and RHS 144B, becoming indistinct.
- *Color of veins, lower surface.*—Closest to RHS 144B, becoming indistinct.
- *Pattern of veining.*—Palmate.
- *Petiole color.*—Closest to RHS 144A.
- *Petiole length.*—2.5-8.0 cm.
- *Diameter of petiole.*—0.2-0.3 cm.
- *Texture.*—Pilose, hirsute hairs.

Stem:
- *Quantity of branches.*—6-8 branches extending from base (lateral branches not included in counting).
- *Color of stem.*—Closest to RHS 144A.
- *Length of stem.*—20-70 cm.
- *Diameter.*—About 0.5-0.6 cm.
- *Length of internodes.*—1.5-7.0 cm.
- *Texture.*—Hirsute, pilose hairs.

Peduncle:
- *Color of peduncle.*—Closest to RHS 144A.
- *Length of peduncle.*—6.0-14.0 cm.
- *Peduncle diameter.*—0.3-0.4 cm.
- *Texture.*—Hirsute.

Pedicel:
- *Color of pedicel.*—Closest to RHS 144A and RHS 144B.
- *Length of pedicel.*—3.0-3.5 cm.
- *Diameter of pedicel.*—0.15-0.2 cm.
- *Texture.*—Pilose.

Bud (just before opening):
- *Color.*—Margins and apex closest to RHS 66A and RHS 66B, but much whiter to white in the middle.
- *Length.*—About 1.5 cm.
- *Width.*—0.9-1.1 cm.
- *Shape.*—Elliptical.

Inflorescence:
- *Type.*—Umbel, semi-spherical.
- *Lastingness of individual flowers.*—7-9 days at 18° C. temperature.
- *Number of inflorescences per plant.*—8 mature and 25 immature umbels in various stages.
- *Fragrance.*—None.
- *Umbel diameter.*—About 8.0-10.0 cm.
- *Umbel depth.*—About 5.5-6.0 cm.

Corolla:
- *Form.*—Double.
- *Number of petals.*—25-35, including staminoids.
- *Diameter of flower.*—About 5 cm.
- *Depth of flower.*—2.0-2.5 cm.
- *Color upper petals, upper surface.*—Closest to RHS 66A and RHS 66B, with darker purple-red marking (stripes and dots) at base and in the middle.
- *Color upper petals, lower surface.*—Closest to RHS 66A and RHS 66B (margins) but much whiter to white in the middle.
- *Length of upper petals.*—2.8-3.2 cm.
- *Width of upper petals.*—1.7-1.9 cm.
- *Color lower petals, upper surface.*—Closest to RHS 66A and RHS 66B.
- *Color lower petals, lower surface.*—Closest to RHS 66A and RHS 66B (margins) but much whiter to white in the middle.
- *Length of lower petals.*—2.6-2.8 cm.
- *Width of lower petals.*—1.4-1.6 cm.
- *Petal shape.*—Obovate to spatulate.
- *Apex shape.*—Rounded.
- *Margin.*—Entire.
- *Base.*—Attenuate.
- *Petal texture.*—Pilose.

Calyx:
- *Number of sepals.*—5.
- *Color of sepals.*—Closest to RHS 144A mottled with anthocyanins of colors RHS 66A.
- *Length of sepals.*—1.4-1.6 cm.
- *Width of sepals.*—0.4-0.6 cm.
- *Sepal shape.*—Lanceolate to enciform.
- *Apex shape.*—Acute.
- *Margins.*—Entire.
- *Texture, upper surface.*—Pilose.
- *Lower surface.*—Pilose.

Reproductive organs:

Gynoecium:
- *Pistil.*—1.
- *Length.*—1-1.1 cm.
- *Style color.*—Closest to RHS 145D.
- *Style length.*—0.5-0.6 cm.
- *Stigma color.*—Closest to RHS 66A (apex) while closest to RHS 144A and RHS 144B at base.

*Ovary color*.—Closest to RHS 145A.
*Ovary length*.—0.4-0.5 cm.
*Ovary diameter*.—About 0.3 cm.

Androecium:

*Number of stamens*.—5.
*Color of filaments*.—Closest to RHS 155C.
*Length filaments*.—1.0-1.1.
*Anther color*.—Closest to RHS 12A and RHS 13A.
*Length of anthers*.—About 0.3 cm.
*Color of pollen*.—Not detected.
*Pollen amount*.—None.
*Fertility/seed set*.—Has not been determined to date.
*Disease/pest resistance*.—Has not been determined to date.

What is claimed is:

1. A new and distinct variety of *Pelargonium* plant named 'PEQZ0066' substantially as illustrated and described herein.

* * * * *